United States Patent [19]

Hickox et al.

[11] Patent Number: 5,018,395
[45] Date of Patent: May 28, 1991

[54] GAS SAMPLING DEVICE WITH IMPROVED MIXED FLOW FAN

[75] Inventors: Richard M. Hickox, Ross Township, Allegheny County; William P. Spohn, Swissvale; David J. D'Amico, Oakmont, all of Pa.

[73] Assignee: Bacharach, Inc., Pittsburgh, Pa.

[21] Appl. No.: 477,233

[22] Filed: Feb. 8, 1990

[51] Int. Cl.⁵ ............................................. G01N 1/24
[52] U.S. Cl. .................................. 73/864.34; 73/23.2
[58] Field of Search ............... 73/864.34, 23.2, 31.01, 73/31.02

[56] References Cited

U.S. PATENT DOCUMENTS

| | | | |
|---|---|---|---|
| 1,994,884 | 3/1935 | Chew | 255/1 |
| 2,987,921 | 6/1961 | Kraftson | |
| 3,507,622 | 4/1970 | Tammelin et al. | 73/31.02 X |
| 3,612,039 | 10/1971 | Falk | 73/23.2 X |
| 3,680,388 | 8/1972 | Critchley et al. | |
| 3,817,100 | 6/1974 | Anderson et al. | 73/864.34 X |
| 3,861,195 | 1/1975 | von Hagen | 73/23.2 |
| 3,933,029 | 1/1976 | Rabeneeker et al. | 73/864.34 X |
| 3,976,450 | 8/1976 | Morcote et al. | 73/31.02 X |
| 4,032,395 | 6/1977 | Burnette | 176/19 LD |
| 4,470,316 | 9/1984 | Jiskoot | 73/863.84 |
| 4,594,903 | 6/1986 | Johnson | 73/863.83 |
| 4,653,334 | 3/1987 | Capone | 73/863.81 |
| 4,739,647 | 4/1988 | Monticelli, Jr. | 73/23.2 |
| 4,785,658 | 11/1988 | Jackson | 73/31.01 |
| 4,839,014 | 6/1989 | Park et al. | 73/23.2 X |
| 4,868,546 | 9/1989 | Pumbeck | 73/31.02 X |

*Primary Examiner*—Tom Noland
*Attorney, Agent, or Firm*—Webb, Burden, Ziesenheim & Webb

[57] ABSTRACT

A gas sampling device including a chamber assembly formed of a chamber base having a chamber top mounted thereto is disclosed. A gas sensor is mounted to the chamber base in fluid communication with a gas flow passage therethrough. A motor is mounted to the lower surface of the chamber base and has a shaft extending through the chamber base. A fan is mounted onto the motor shaft within the chamber housing. An inlet flow passage extends through the chamber top above the center of the fan and an outlet flow passage extends through the chamber top above the gas flow passage. The fan and the chamber top are provided with a particular configuration to provide for efficient and smooth flows of gas through the housing and to the sensor.

26 Claims, 3 Drawing Sheets

GAS SAMPLING DEVICE WITH IMPROVED MIXED FLOW FANS

BACKGROUND OF THE INVENTION

1. Field Of The Invention

This invention relates to the detection of gases and, more particularly, to gas sampling devices which draw a sample gas to a sensor within the device.

2. Background Art

Devices for sampling a gas and determining the concentration of a particular gas in the sample gas are well-known. Such gas sampling devices generally include a gas sensor, which develops an electrical signal in response to the presence of a particular gas, and circuitry for converting that signal into an output reading. Gas sampling devices often include a pump which draws the sample gas through a probe and causes the gas to pass over the sensor.

Hand-held, battery operated gas sampling devices are also well-known. These devices are used to test for the presence of a particular gas in remote areas or other locations where it is impractical to use larger, bench devices. Hand-held gas sampling devices are commonly used by inspectors to check the operation of furnaces, gas hot water heaters, and devices in which excess concentrations of carbon monoxide, sulfur dioxide, oxygen or the like is an indication of a problem.

It is known to use a reciprocating pump to draw gas into a sampling device. However, reciprocating pumps have a number of drawbacks. Specifically, the gas flowing from a reciprocating pump exhibits pressure pulsations resulting from the reciprocation of a diaphragm internal to the pump. Such pressure pulsations interfere with the operation of many gas sensors, such as electrochemical gas sensors which are extremely pressure sensitive. Moreover, a reciprocating pump requires an expensive and powerful motor and is sensitive to dirt and liquid.

A squirrel cage type of centrifugal fan has also been used to draw a sample gas into a gas sampling device. However, such a fan develops only a low pressure potential and cannot draw a sample gas against a large pressure. In addition, the structure permits residual gas to remain after a test, which could adversely affect the reading obtained from a subsequent test. Moreover, the squirrel cage fan draws far too much gas volume and uses too much energy from the power source for the device.

It is an object of the present invention to provide a gas sampling device which positively draws gas to the gas sensor, but which overcomes the disadvantages of the prior art. It is an objective to provide a gas sampling device which requires an inexpensive motor, which maintains little residual gas, which draws gas at a steady pressure, which is insensitive to dirt and water, which is relatively maintenance free and which produces a larger pressure differential than the squirrel cage fan, yet draws only a small amount of sample gas and is energy efficient in operation.

SUMMARY OF THE INVENTION

Accordingly, we have developed a gas sampling device which includes a chamber including a chamber top mounted to a chamber base. The chamber base has a gas flow passage extending therethrough and into the chamber. A circular fan is positioned with the chamber and is spaced from and directs gas flows toward the gas flow passage. The fan is rotatable in a plane substantially parallel to an upper surface of the chamber base. A motor is mounted to a lower surface of the chamber base and has a shaft extending perpendicularly through the chamber base and attached to the fan. A gas sensor is mounted to the lower surface of the chamber base and is in fluid communication with the gas flow passage. An inlet flow passage extends through the chamber top above the fan and is oriented substantially perpendicular thereto. In addition, an outlet flow passage extends through the chamber top above the gas flow passage.

In accordance with one embodiment of this invention, the chamber top includes a fan housing surrounding but spaced from an outer perimeter of the fan. The chamber top also includes a gas tunnel housing extending tangentially from the fan housing to the gas flow passage. The fan housing has an inner wall which has a linearly increasing, outward spiral shape in which the spacing between the outer perimeter of the fan and the inner wall gradually increases, in the direction of rotation of the fan, from a minimum in an area following the gas tunnel housing, to a maximum in a transition area between the fan housing and the gas tunnel housing. The spacing between the side of the fan and the inner wall of the fan housing is about 6-12%, preferably 8%, of the outer diameter of the fan in the area immediately following the gas tunnel housing. The spacing between an inner upper surface of the fan housing and a top edge of the fan blades is about 6-12%, preferably 8%, of the outer diameter of the fan.

In accordance with a second embodiment of this invention, the fan includes a circular bottom member having a flat central area and a tapered peripheral area extending from the central area toward the chamber base. The fan also includes a plurality of spaced fan blades, alternating between long fan blades and short fan blades, which extend substantially vertically along an upper surface of the bottom member. The fan blades also extend radially along the tapered peripheral area and into the flat central area. The fan blades have tips which are spaced from a center of the fan, with the long fan blades extending further toward the center of the fan than the short fan blades. The fan can also include along its outer perimeter a thin skirt extending toward but spaced from the chamber base. It is also preferred that the space between the tips of adjacent long fan blades be about the same as the space between the tips of adjacent long and short fan blades.

It is preferred that the motor used to power the fan be a direct current motor capable of rotating at least 7,000 rpm. The gas sensor can be any of the known types of gas sensors, including electrochemical, catalytic combustible, solid state and electro-optic gas sensors.

The gas sampling device can be advantageously used with a variety of probes. It is particularly advantageous with a probe which includes both an inlet passageway for supplying gas to the inlet flow passage of the device and also an outlet passageway for exhausting gas from the outlet flow passage of the device back to the atmosphere or the source of the sample gas.

DESCRIPTION OF THE PREFERRED EMBODIMENTS

Figure 1:
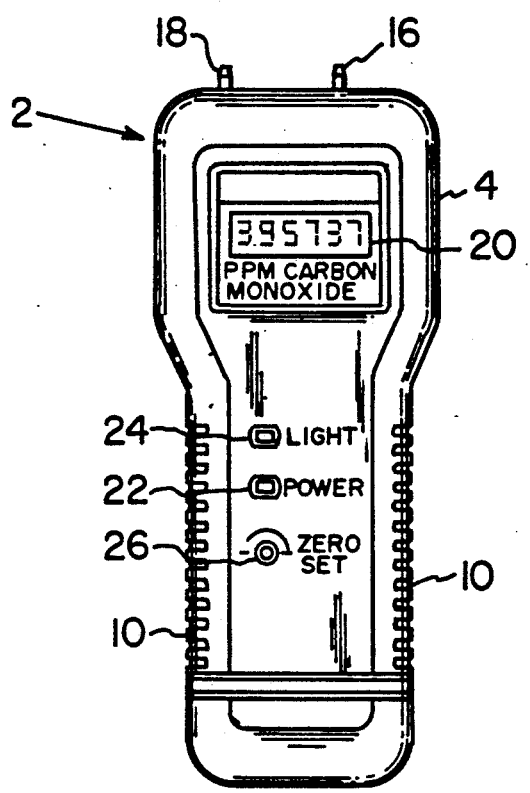
FIG. 1 is a front elevational view of a gas sampling device in accordance with the present invention.
Figure 2:
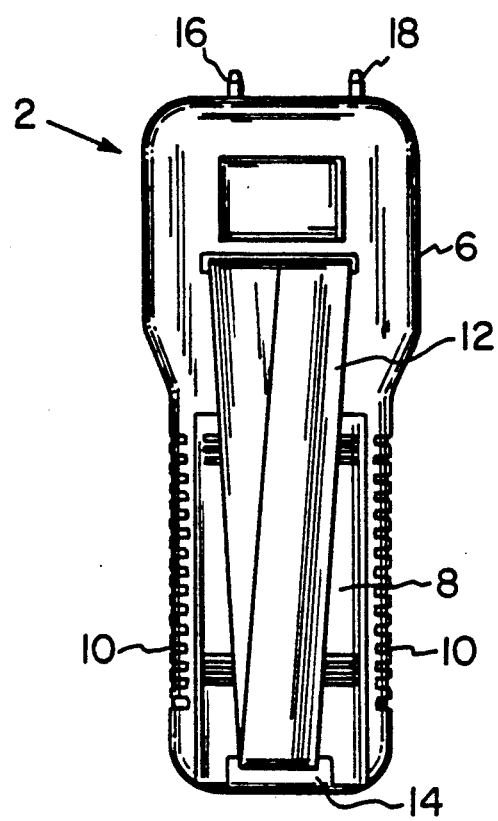
FIG. 2 is a rear elevational view of the gas sampling device shown in FIG. 1.
Figure 3:
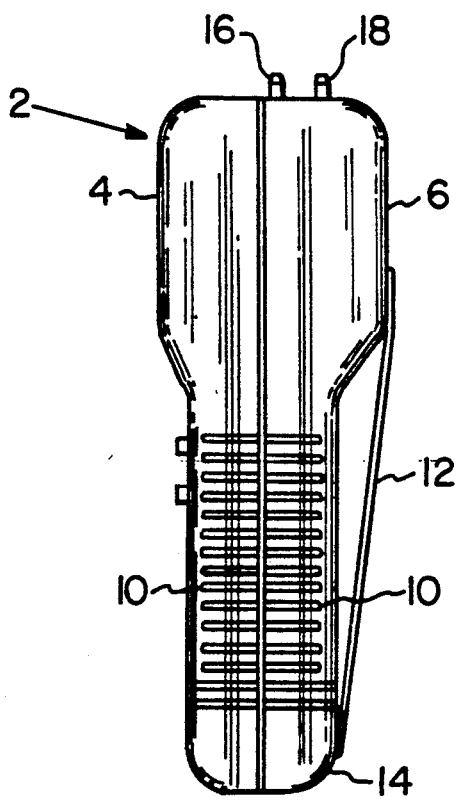
FIG. 3 is a side elevational view of the gas sampling device shown in FIG. 1.
Figure 5:
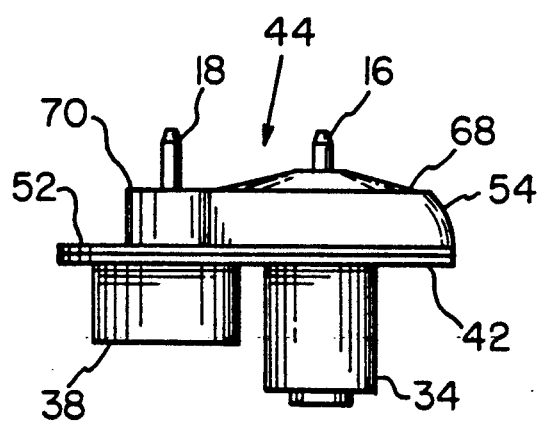
FIG. 5 is a front elevational view of the chamber assembly, motor and sensor included in the gas sampling device shown in FIG. 4.

A portable, battery operated gas sampling device 2 in accordance with the present invention is shown in FIGS. 1-3. The gas sampling device 2 includes a front housing 4 connected to a rear housing 6. The housings 4, 6 contain the working elements of the gas sampling device 2. The rear housing 6 includes a battery compartment therein which is sealed by a removable battery compartment cover 8. The front and rear housings 4, 6 are shown having a wide upper portion and narrow lower portion, but other shapes and configurations can be readily used. The lower portions of the front and rear housings 4, 6 can include grip areas 10 to provide for ease in handling the gas sampling device 2. In addition, the rear housing 6 has an elastic strap 12 extending from an upper portion thereof to a lower portion of the battery compartment cover 8. The strap 12 can be removably secured to the battery compartment cover 8 by a clip 14 or the like. The strap 12 will snugly, yet comfortably, hold a user's hand in place around the grip areas 10 of the gas sampling device 2 and keep the device 2 from being accidentally dropped.

The upper portion of the gas sampling device 2 includes through the rear housing 6 an inlet nipple 16 for directing the inlet flow of a sample gas under test, and an outlet nipple 18 for directing the sample gas either back to its original source or to atmosphere. The gas sampling device 2 develops a signal indicative of the concentration of a particular gas and the concentration is shown on a liquid crystal display 20 or other known display or read out means. The front housing 4 can also include convenient control buttons. As shown, the front housing 4 includes a power switch 22, a light switch 24 for the display 20, and a potentiometer 26. The potentiometer 26 is a well-known element in gas sampling devices and is used to calibrate the device before a sample gas is passed therethrough.

Figure 4:
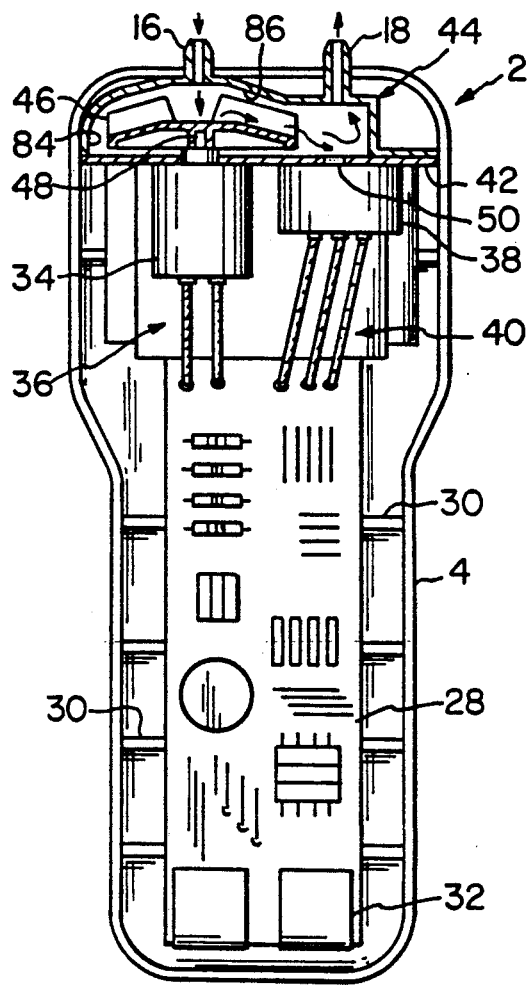
FIG. 4 is a rear elevational view of the gas sampling device shown in FIG. 1 with the rear housing removed.

Referring to FIG. 4, there is shown the working elements inside the gas sampling device 2 shown in FIGS. 1-3. The device 2 includes a printed circuit board 28 supported by a plurality of bosses 30 formed integrally with the front housing 4. Similar bosses are formed in the rear housing 6 and will snugly support the printed circuit board 28 within the gas sampling device 2. A lower end of the printed circuit board 28 includes a pair of battery contacts 32. Opposing battery contacts can be provided either on an upper end of the printed circuit board 28 or on the rear housing 6. The gas sampling device 2 also includes a motor 34 which is electrically connected to the printed circuit board 28 by a pair of motor wires 36. The motor 34 is preferably a small DC motor capable of rotating at speeds of 7,000 rpm or higher. The gas sampling device 2 also includes a gas sensor 38 which is electrically connected to the printed circuit board 28 by a plurality of sensor wires 40. For example, the sensor 38 can be a three electrode electrochemical gas sensor which includes reference, sensing and cathode electrodes. Each of these electrodes requires a separate wire to the printed circuit board 28. Thus, FIG. 4 shows three sensor wires 40 extending from the sensor 38 to the printed circuit board 28. The sensor 38 can also be a catalytic combustible gas sensor, a solid state gas sensor or an electro-optic gas sensor.

A gas chamber formed of a substantially planar chamber base 42 and a chamber top 44 is provided within the gas sampling device 2 above the motor 34 and the sensor 38 and beneath the top of the gas sampling device 2. A circular fan 46 is positioned in the gas chamber formed by the chamber top 44 and chamber base 42, and rotates in a plane substantially parallel to an upper surface of the chamber base 42. The motor 34 is mounted on a lower surface of the chamber base 42 and is connected to the fan 46 by a motor shaft 48 which extends perpendicularly through the chamber base 42. A gas flow passage or hole 50 extends through the chamber base 42 immediately above and in fluid communication with the gas sensor 38 which is mounted on the lower surface of the chamber base 42.

Figure 6:
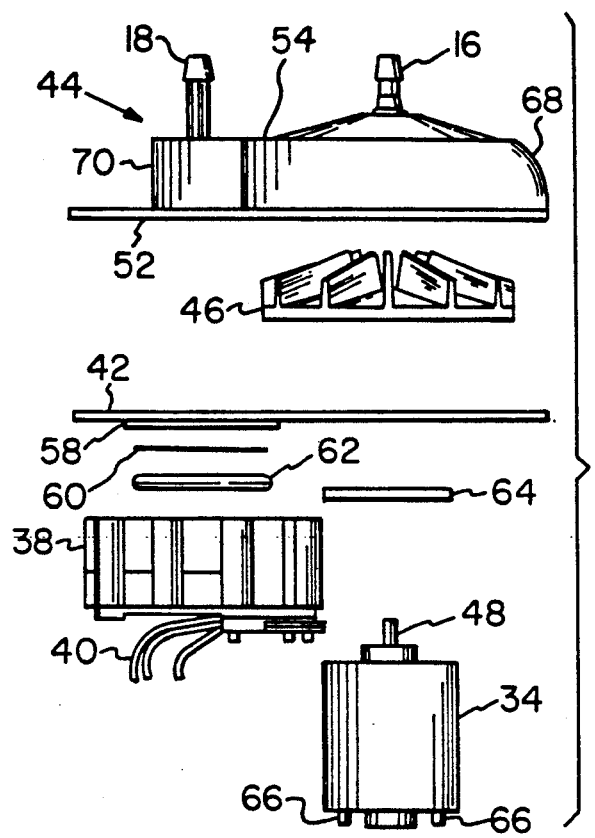
FIG. 6 is an exploded view of the elements shown in FIG. 5.
Figure 7:
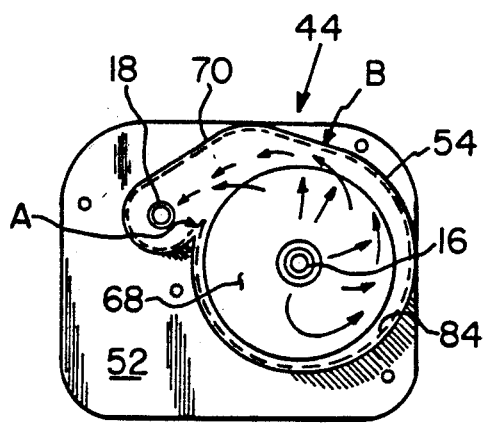
FIG. 7 is a top plan view of the chamber assembly shown in FIG. 5.
Figure 8:
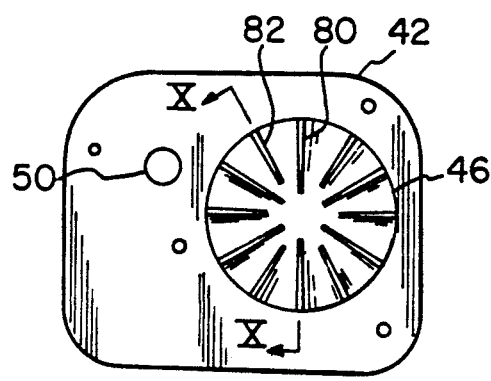
FIG. 8 is a plan view of the chamber assembly shown in FIG. 5 with the top removed.

Referring to FIGS. 4-9, the chamber top 44 includes a bottom flange 52 and a raised housing 54. The inlet nipple 16 is connected to the raised housing 54 and has a flow passage extending therethrough to the interior of the raised housing 54. The inlet nipple 16 forms an inlet flow passage through the chamber top 54 and is positioned immediately above the center of the fan 46 and is oriented substantially perpendicular thereto. The outlet nipple 18 is also connected to the raised housing 54 and has a flow passage extending therethrough to the interior of the raised housing 54. The outlet nipple 18 provides an outlet flow passage extending through the chamber top 54 and is positioned above the gas flow passage 50. As shown in FIG. 8, the fan 46 is mounted above the upper surface of the chamber base 42 and is spaced apart from the gas flow passage 50.

The chamber base 42 is essentially a rectangular plate with rounded corners. The flange 52 of the chamber top 44 extends outwardly by a particular amount and to a particular configuration such that the chamber top 44 has an outer shape matching that of the chamber base 42. In this manner, the chamber top 44 can be securely mounted, for example with fasteners, to the chamber base 42 to form the chamber assembly.

The chamber assembly 42, 44, the fan 46, the motor 34, and the gas sensor 38 are shown more clearly in FIG. 6. The lower surface of the chamber base 42 includes cylindrical ridge 58 surrounding the gas flow passage 50. This cylindrical ridge 58 holds a thin, circular membrane 60 which is positioned above the inlet to the gas sensor 38. An O-ring 62 is positioned between the circular membrane 60 and the gas sensor 38, and the gas sensor 38 is secured to the chamber assembly 42, 44 by bolts or the like. The circular membrane 60 is a known device for controlling the flow of gas to the gas sensor 38. Similarly, the fan 46 is positioned above the upper surface of the chamber base 42, and the shaft 48 of the motor 34 passes through the chamber base 42 and is connected to the fan 46. A cushioning gasket 64 can be positioned between the motor 34 and the lower surface of the chamber base 42 to reduce vibration and provide for a secure fit. Likewise, the motor is secured to the chamber base 42 by suitable fasteners. The motor 34 shown in FIG. 6 includes a pair of motor wire contacts 66 to which are connected the motor wires 36 shown in FIG. 4. Finally, the chamber top 44 is secured to the chamber base 42 by suitable fasteners.

Figure 9:
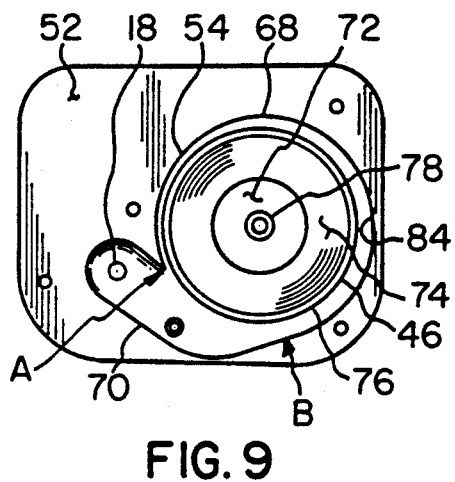
FIG. 9 is a bottom plan view of the chamber top with a fan positioned therein.
Figure 10:
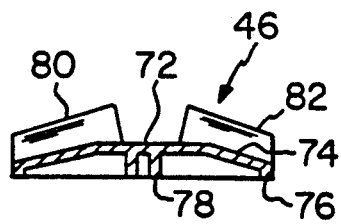
FIG. 10 is a section taken along lines X—X in FIG. 8.
Figure 11:
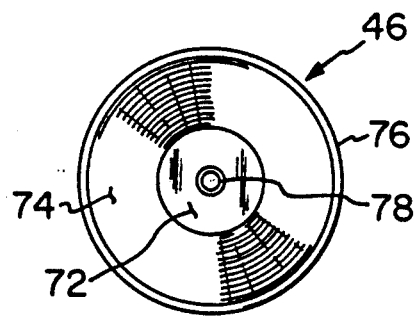
FIG. 11 is a bottom plan view of the fan shown in FIG. 8.

As shown more clearly in FIGS. 7-9, the raised housing 54 in the chamber top 44 includes a raised fan housing 68 which surrounds but is spaced from the fan 46. The raised housing 54 also includes a gas tunnel housing 70 integral therewith which extends tangentially from the fan housing 68 to the gas flow passage 50 when the chamber top 44 is mounted to the chamber base 42. The inlet nipple 16 is positioned in approximately the center of the fan housing 68 and is oriented to direct gas flows perpendicular therethrough to the center of the fan 46. Similarly, the outlet nipple 18 is positioned in the gas tunnel housing 70 above the gas flow passage 50.

In accordance with the present invention, the fan housing 68 of the raised housing 54 includes a particular spacing between the outer perimeter of the fan 46 and the inner wall 84 of the fan housing 68. In particular, the fan housing 68 includes an inner wall 84 which has a linearly increasing, outward spiral shape, also called an involute spiral shape, in which the spacing between the outer perimeter of the fan 46 and the inner wall 84 gradually increases, in the direction of rotation of the fan 46, from a minimum in the area following the gas tunnel housing 70 to a maximum at a transition area between the fan housing 68 and the gas tunnel housing 70. This is shown more clearly in both FIGS. 7 and 9, with the approximate locations of the minimum and maximum spacings shown by reference letters A and B, respectively. The spacing between the outer perimeter of the fan 46 and the inner wall 84 of the fan housing 68 should be about 6 to 12% of the outer diameter of the fan 46 at the minimum spacing. It is preferred that the spacing be about 8% of the outer diameter of the fan 46 at this location. In addition, it is preferred that the spacing between an inner upper surface 86 of the fan housing 68 and a top edge of the fan 46 be about 6 to 12%, preferably about 8%, of the outer diameter of the fan 46. By providing these spacings between the fan 46 and the fan housing 68, the gas will flow smoothly and efficiently through the chamber assembly and to the sensor 38 as the fan 46 rotates.

The fan 46 is shown in detail in FIGS. 8-11. The fan 46 can be referred to as a mixed flow fan because, as will be explained hereinafter in more detail, the flows through the fan 46 are in both radial and axial directions. The fan 46 includes a circular bottom member having a flat central area 72 and a tapered peripheral area 74 extending outwardly from the central area 72 toward the chamber base 42 when the fan 46 is assembled on the motor shaft 48. The peripheral edge of the fan 46 can also include a downwardly oriented skirt 76 around its circumference. The bottom surface of the central area 72 of the fan 46 includes a mounting collar 78 which is adapted to securely receive the shaft 48 of the motor 34. The mounting collar 78 preferably does not extend downwardly below the bottom edge of the skirt 76 of the fan 46.

The fan 46 also includes a plurality of spaced fan blades, alternating between long fan blades 80 and short fan blades 82, which are oriented substantially vertical to the upper surface of the bottom member of the fan 46 and extend generally radially therealong. As shown more clearly in FIG. 10, the fan blades 80, 82 extend from the peripheral edge of the fan 46 toward the center of the fan 46 along the tapered peripheral area 74 and into the flat central area 72. However, the tips of the fan blades 80, 82 are spaced from the center of the fan 46 to provide an area in the middle of the flat central area 72 which has no fan blades. The long fan blades 80 extend further toward the center of the fan 46 than the short blades 82. It is preferred that the spacing between the tips of adjacent long fan blades 80 be approximately the same as the spacing between the tips of an adjacent long fan blade 80 and short fan blade 82. The particular arrangement of the fan blades 80, 82, with the staggered arrangement in the center of the fan 46, provides for smooth gas flow through the fan 46 at a proper pressure and with no choking of the gas flow.

In operation, the motor 34 rotates the fan 46 within the fan housing 68 and creates a vacuum which draws gas axially through the inlet nipple 16 and into the central area 72 of the fan 46. The gas then flows radially along the fan blades 80, 82 toward the inner wall 84 of the fan housing 68 and then flows along the inner wall 84 generally tangential to the skirt 76 of the fan 46. The gas then flows into the gas tunnel housing 70 where it passes into the gas flow passage 50 in the chamber base 42 and comes in contact with the gas sensor 38 located therebeneath. The gas sensor 38 detects the concentration of a particular gas, if present, and develops a signal supplied to the printed circuit board 28. The circuitry on the printed circuit board 28 converts this signal into a reading on the liquid crystal display 20. The tested gas then passes out of the gas tunnel housing 70 through the outlet nipple 18. It is preferred that the power to the motor 34 be supplied through a voltage regulator on the printed circuit board 28, rather than directly from the batteries, to prevent variations in fan speed due to a decrease in battery strength. This will keep pressure variation on the gas sensor 38 to a minimum.

Figure 12:
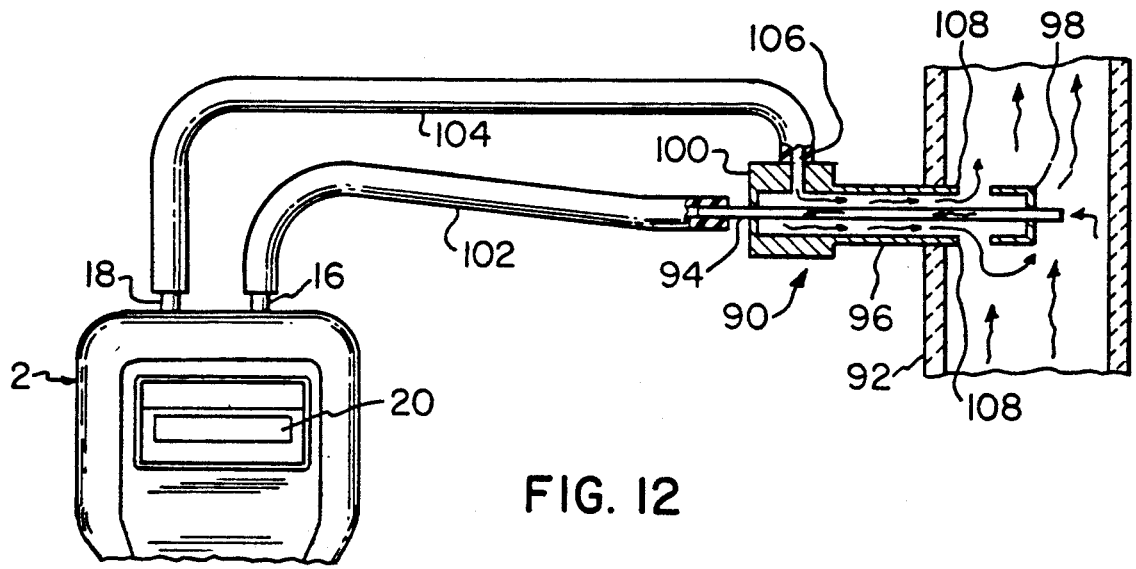
FIG. 12 is a side elevational view, partially in section, of the gas sampling device of FIG. 1 connected to a flue gas sampling probe in accordance with the present invention.

A system for sampling a flue gas, using the gas sampling device 2 discussed above, is shown in FIG. 12. As shown, a probe 90 is inserted through the side of a flue 92 which has flue gas flowing therethrough. The probe 90 is constructed of an inner cylindrical tube 94 which is surrounded by a concentric outer tube 96 spaced therefrom. The spacing between the outer surface of the inner tube 94 and the inner surface of the outer tube 96 provides an annular chamber therebetween. A first end 98 of the outer tube 96 located within the flue 92 is closed off and the inner tube 94 extends therethrough for a short distance into the flue 92. Likewise, a second end 100 of the outer tube 98 is closed off and the inner tube 94 extends outwardly therethrough for a short distance. An inlet hose 102 extends from the inlet nipple 16 of the gas sampling device 2 and is connected to the inner tube 94 at the second end 100 of the outer tube 96 of the probe 90. Similarly, an outlet hose 104 is connected from the outlet nipple 18 of the gas sampling device 2 and is connected to an outlet fitting 106 on the probe 90 near the second end 100. The outlet fitting 106 is in fluid communication with the annular chamber between the outer tube 96 and the inner tube 94. The outer tube 96 also includes a plurality of exhaust openings 108 therethrough adjacent the first end 98 and in fluid communication with the annular chamber between the inner tube 94 and the outer tube 96.

By this arrangement, the sample gas can be drawn from the flue 92 through the inner tube 94, through the inlet hose 102 and into the gas sampling device 2 through the inlet nipple 16. The tested gas will then pass from the gas sampling device 2 through the outlet nipple 18 and outlet hose 104, through the outlet fitting 106 and into the annular chamber between the inner tube 94 and the outer tube 96. The gas will then flow between the inner tube 94 and outer tube 96 to the exhaust openings 108 in the outer tube 96, where the gas will pass into the flue 92 and be exhausted along with the unsampled flue gas. By providing exhaust openings 108 in the flue 92, the gas sampling device 2 need only provide a differential pressure to overcome the net pressure loss in the flow path from the end of the inner tube 94 in the flue 92 and back to the exhaust openings 108 in the probe 90. The gas sampling device 2 need not provide the large pressure necessary to overcome the large, negative pressure often found in a flue gas. Of course, the gas sampling device 2 can also be used with standard probes and the use of an exhaust path from the outlet nipple 18 need not always be provided.

The gas sampling device of the present invention provides an arrangement which is relatively inexpensive to manufacture and has low power consumption, permitting a less powerful and inexpensive motor to be used and giving the batteries a longer operating life. The smooth flow of gas through the chamber eliminates pressure variations to the sensor. Only an amount of gas sufficient to conduct the test is drawn into the device. The structure permits little residual gas in the device, it is relatively insensitive to contaminants and it is easy to clean and maintain.

Having described herein the presently preferred embodiments of the present invention, it is to be understood that the invention may be otherwise embodied within the scope of the appended claims.

We claim:

1. A gas sampling device comprising:
   (a) a chamber including a chamber top mounted to a chamber base, with the chamber base having a gas flow passage extending therethrough and into the chamber;
   (b) a circular fan positioned within the chamber and spaced from and directing gas flows toward the gas flow passage, with the fan rotatable in a plane substantially parallel to an upper surface of the chamber base;
   (c) a motor mounted to a lower surface of the chamber base and having a shaft extending perpendicularly through the chamber base and attached to the fan;
   (d) a gas sensor mounted to the lower surface of the chamber base and in fluid communication with the gas flow passage;
   (e) an inlet flow passage extending through the chamber top above the fan and oriented substantially perpendicular thereto; and
   (f) an outlet flow passage extending through the chamber top above the gas flow passage, with the chamber top including a fan housing surrounding but spaced from an outer perimeter of the fan and a gas tunnel housing extending tangentially from the fan housing to the gas flow passage, with the fan housing having an inner wall which has a linearly increasing, outward spiral shape in which the spacing between the outer perimeter of the fan and the inner wall gradually increases, in the direction of rotation of the fan, from a minimum in an area following the gas tunnel housing, to a maximum in a transition area between the fan housing and the gas tunnel housing.

2. The gas sampling device of claim 1 wherein the spacing between the outer perimeter of the fan and the inner wall of the fan housing is about 6-12% of the outer diameter of the fan in the area following the gas tunnel housing.

3. The gas sampling device of claim 1 wherein the spacing between the outer perimeter of the fan and the inner wall of the fan housing is about 8% of the outer diameter of the fan in the area following the gas tunnel housing.

4. The gas sampling device of claim 1 wherein the spacing between an inner upper surface of the fan housing and a top edge of the fan is about 6-12% of the outer diameter of the fan.

5. The gas sampling device of claim 1 wherein the spacing between an inner upper surface of the fan housing and a top edge of the fan is about 8% of the outer diameter of the fan.

6. The gas sampling device of claim 1 wherein the spacing between the outer perimeter of the fan and the inner wall of the fan housing is about 6-12% of the outer diameter of the fan in the area following the gas tunnel housing and wherein the spacing between an inner upper surface of the fan housing and a top edge of the fan is about 6-12% of the outer diameter of the fan.

7. The gas sampling device of claim 1 wherein the fan includes a circular bottom member having a flat central area and a tapered peripheral area extending from the central area toward the chamber base, with the fan further including a plurality of spaced fan blades, alternating between long fan blades and short fan blades, extending substantially vertically along an upper surface of the bottom member, with the fan blades extending radially along the tapered peripheral area and into the flat central area and having tips which are spaced from a center of the fan, with the long fan blades extending further toward the center of the fan than the short fan blades.

8. The gas sampling device of claim 7 wherein the fan includes along its outer perimeter a thin skirt extending toward but spaced from the chamber base.

9. The gas sampling device of claim 7 wherein the space between the tips of adjacent long fan blades in the central area is about the same as the space between the tips of adjacent long and short fan blades in the central area.

10. The gas sampling device of claim 1 wherein said motor is a direct current motor capable of rotating at least 7,000 rpm.

11. The gas sampling device of claim 1 wherein said gas sensor is selected from the group consisting of electrochemical, catalytic combustible, solid state and electro-optic gas sensors.

12. The gas sampling device of claim 1 further including a probe for supplying a sample gas thereto, said probe including an inlet passageway supplying gas to the inlet flow passage and an outlet passageway exhausting gas from the outlet flow passage.

13. The gas sampling device of claim 12 wherein said probe includes an inner tube surrounded by an outer tube spaced therefrom, with each end of the outer tube closed off and with the inner tube extending outwardly beyond each end, and with exhaust openings through said outer tube at one end thereof, and with the inner tube supplying gas to said inlet flow passage and with the space between the inner and outer tubes carrying gas from the outlet flow passage.

14. A gas sampling device comprising:
(a) a chamber including a chamber top mounted to a chamber base, with the chamber base having a gas flow passage extending therethrough and into the chamber;
(b) a circular fan positioned within the chamber and spaced from and directing gas flows toward the gas flow passage, with the fan rotatable in a plane substantially parallel to an upper surface of the chamber base;
(c) a motor mounted to a lower surface of the chamber base and having a shaft extending perpendicularly through the chamber base and attached to the fan;
(d) a gas sensor mounted to the lower surface of the chamber base and in fluid communication with the gas flow passage;
(e) an inlet flow passage extending through the chamber top above the fan and oriented substantially perpendicular thereto; and
(f) an outlet flow passage extending through the chamber top above the gas flow passage, with the fan including a circular bottom member having a flat central area and a tapered peripheral area extending from the central area toward the chamber base, with the fan further including a plurality of spaced fan blades, alternating between long fan blades and short fan blades, extending substantially vertically along an upper surface of the bottom member, with the fan blades extending radially along the tapered peripheral area and into the flat central area and having tips which are spaced from a center of the fan, with the long fan blades extending further toward the center of the fan than the short fan blades.

15. The gas sampling device of claim 14 wherein the fan includes along its outer perimeter a thin skirt extending toward but spaced from the chamber base.

16. The gas sampling device of claim 14 wherein the space between the tips of adjacent long fan blades in the central area is about the same as the space between the tips of adjacent long and short fan blades in the central area.

17. The gas sampling device of claim 14 wherein the chamber top includes a fan housing surrounding but spaced from an outer perimeter of the fan and a gas tunnel housing extending tangentially from the fan housing to the gas flow passage, with the fan housing having an inner wall which has a linearly increasing, outward spiral shape in which the spacing between the outer perimeter of the fan and the inner wall gradually increases, in the direction of rotation of the fan, from a minimum in an area following the gas tunnel housing, to a maximum in a transition area between the fan housing and the gas tunnel housing.

18. The gas sampling device of claim 17 wherein the spacing between the outer perimeter of the fan and the inner wall of the fan housing is about 6–12% of the outer diameter of the fan in the area following the gas tunnel housing.

19. The gas sampling device of claim 17 wherein the spacing between the outer perimeter of the fan and the inner wall of the fan housing is about 8% of the outer diameter of the fan in the area following the gas tunnel housing.

20. The gas sampling device of claim 17 wherein the spacing between an inner upper surface of the fan housing and a top edge of the fan is about 6–12% of the outer diameter of the fan.

21. The gas sampling device of claim 17 wherein the spacing between an inner upper surface of the fan housing and a top edge of the fan is about 8% of the outer diameter of the fan.

22. The gas sampling device of claim 17 wherein the spacing between the outer perimeter of the fan and the inner wall of the fan housing is about 6–12% of the outer diameter of the fan in the area following the gas tunnel housing and wherein the spacing between an inner upper surface of the fan housing and a top edge of the fan is about 6–12% of the outer diameter of the fan.

23. The gas sampling device of claim 14 wherein said motor is a direct current motor capable of rotating at least 7,000 rpm.

24. The gas sampling device of claim 14 wherein said gas sensor is selected from the group consisting of electrochemical, catalytic combustible, solid state and electro-optic gas sensors:

25. The gas sampling device of claim 14 further including a probe for supplying a sample gas thereto, said probe including an inlet passageway supplying gas to the inlet flow passage and an outlet passageway exhausting gas from the outlet flow passage.

26. The gas sampling device of claim 25 wherein said probe includes an inner tube surrounded by an outer tube spaced therefrom, with opposite ends of the outer tube closed off and with the inner tube extending outwardly beyond each end, and with exhaust openings through said outer tube at one end thereof, and with the inner tube supplying gas to said inlet flow passage and with the space between the inner and outer tubes carrying gas from the outlet flow passage to the exhaust openings.

* * * * *

UNITED STATES PATENT AND TRADEMARK OFFICE
CERTIFICATE OF CORRECTION

PATENT NO. : 5,018,395

DATED : May 28, 1991

INVENTOR(S) : Richard M. Hickox, William P. Spohn and David J. D'Amico

It is certified that error appears in the above-identified patent and that said Letters Patent is hereby corrected as shown below:

Column 1 Line 3 "FAN5" should read --FAN--.

Column 2 Line 62 after "or" insert --to--.

Claim 24 Line 39 Column 10 "sensors:" should read --sensors.--.

Signed and Sealed this

Seventeenth Day of September, 1991

*Attest:*

HARRY F. MANBECK, JR.

*Attesting Officer*   *Commissioner of Patents and Trademarks*